(12) United States Patent
Wright et al.

(10) Patent No.: US 9,895,689 B2
(45) Date of Patent: Feb. 20, 2018

(54) ASEPTIC PROCESSING WORKSTATION

(71) Applicant: BIOQUELL UK LIMITED, Andover (GB)

(72) Inventors: Thomas James Wright, Knaphill (GB); Neil Pomeroy, Compton (GB)

(73) Assignee: BIOQUELL UK LIMITED, Andover (GB)

( * ) Notice: Subject to any disclaimer, the term of this patent is extended or adjusted under 35 U.S.C. 154(b) by 120 days.

(21) Appl. No.: 14/403,499

(22) PCT Filed: Mar. 14, 2013

(86) PCT No.: PCT/GB2013/050631
§ 371 (c)(1),
(2) Date: Nov. 24, 2014

(87) PCT Pub. No.: WO2013/186518
PCT Pub. Date: Dec. 19, 2013

(65) Prior Publication Data
US 2015/0113927 A1    Apr. 30, 2015

(30) Foreign Application Priority Data

Jun. 11, 2012 (GB) .................................. 1210262.0

(51) Int. Cl.
*A61L 2/025* (2006.01)
*B01L 1/02* (2006.01)
(Continued)

(52) U.S. Cl.
CPC ................ *B01L 1/04* (2013.01); *A61L 2/208* (2013.01); *A61L 2202/21* (2013.01); *B01L 2200/0631* (2013.01); *B01L 2300/0681* (2013.01)

(58) Field of Classification Search
CPC ........ A61L 2/0094; A61L 2/025; A61L 2/208; A61L 2202/11; A61L 2202/122;
(Continued)

(56) References Cited

U.S. PATENT DOCUMENTS 3,664,255 A * 5/1972 Kuechler ................ F24C 15/20
126/299 D
3,811,250 A * 5/1974 Fowler, Jr. ............. B01D 46/00
454/56
(Continued)

FOREIGN PATENT DOCUMENTS

CN       102059160 A    5/2011
EP       01268557       10/1989
(Continued)

OTHER PUBLICATIONS

International Search Report and Written Opinion of the International Searching Authority; PCT/GB2013/050631.
(Continued)

*Primary Examiner* — Frank Lawrence, Jr.
*Assistant Examiner* — Minh-Chau Pham
(74) *Attorney, Agent, or Firm* — Maschoff Brennan

(57) ABSTRACT

An aseptic processing workstation can include a processing chamber and an airflow circuit passing through the chamber. The circuit can include an air supply fan, an air return fan and a restriction element. The chamber is located in the circuit between the air supply fan and the air return fan. The restriction element is located in the circuit on the other side of the air supply fan and the air return fan to the chamber. The workstation can include an air inlet fluidly connected at a first connection point to the circuit via inlet valve means. The first connection point is located between the restriction element and the air supply fan. The workstation can include
(Continued)

an air outlet fluidly connected at a second connection point to the circuit via outlet valve means.

20 Claims, 5 Drawing Sheets

(51) Int. Cl.
  *G01M 3/26* (2006.01)
  *B01L 1/04* (2006.01)
  *A61L 2/20* (2006.01)
(58) Field of Classification Search
  CPC .... A61L 2202/13; A61L 2202/14; B01L 1/02; B01L 2300/14; G01M 3/26; C12M 37/00
  USPC ........... 55/385.2; 454/46, 187; 422/111, 120, 422/128
  See application file for complete search history.

(56) References Cited

U.S. PATENT DOCUMENTS

| | | | | |
|---|---|---|---|---|
| 5,487,768 | A * | 1/1996 | Zytka | B01D 46/0023 454/187 |
| 5,730,777 | A * | 3/1998 | Petersen | B25J 21/02 55/310 |
| 5,922,095 | A * | 7/1999 | Hustvedt | B01D 45/06 454/187 |
| 6,033,301 | A * | 3/2000 | Suwa | F24F 3/161 454/187 |
| 6,558,622 | B1 | 5/2003 | Malchesky | |
| 6,790,257 | B2 * | 9/2004 | Jeng | B01D 46/446 55/385.2 |
| 8,034,141 | B2 * | 10/2011 | Polsky | A61L 2/04 312/1 |
| 8,603,217 | B2 * | 12/2013 | Sukhman | B01D 53/04 55/338 |
| 8,658,107 | B2 | 2/2014 | Yokoi et al. | |
| 8,741,227 | B2 | 6/2014 | Yokoi et al. | |
| 8,778,272 | B2 * | 7/2014 | Chan | F24F 3/1603 422/120 |
| 8,915,984 | B2 * | 12/2014 | Kawasaki | B01L 1/04 312/1 |
| 2006/0107635 | A1 * | 5/2006 | Homan | A61G 10/023 55/385.2 |
| 2006/0174596 | A1 * | 8/2006 | Choi | F24F 3/1603 55/467 |
| 2010/0196216 | A1 * | 8/2010 | Yokoi | A61L 2/208 422/128 |
| 2011/0027131 | A1 * | 2/2011 | Yokoi | A61L 2/208 422/128 |
| 2011/0058986 | A1 * | 3/2011 | Yokoi | A61L 2/0094 422/111 |

FOREIGN PATENT DOCUMENTS

| | | |
|---|---|---|
| EP | 2286846 A1 | 2/2011 |
| EP | 2335741 A1 | 6/2011 |
| GB | 2393393 A | 3/2004 |
| HU | 192124 B | 1/1983 |
| JP | H01268557 A | 10/1988 |
| JP | 63278521 A | 11/1988 |
| JP | 2006-116095 A | 11/2006 |
| JP | 2010169366 A | 8/2010 |
| WO | 02/11774 A1 | 2/2002 |
| WO | 2005/094909 | 10/2005 |
| WO | 2010021139 A1 | 2/2010 |
| WO | 2011/022325 A2 | 2/2011 |
| WO | 2012/029875 A1 | 3/2012 |
| WO | 2012/028975 A1 | 8/2012 |

OTHER PUBLICATIONS

Thompson, XP-002698609.
Jinsong Li; Qiushi Li; Na Li; Zhanbo Wen; Wenhui Yang, Biological Safety Protection Cabin, English Translation of CN102059160, May 18, 2011, p. 1-11.
Search Report issued under section 29(2) of the Patent Act dated Feb. 14, 2014 as received in Application No. 11201406693T.
Japanese Office Action in Japanese Application No. 2015-515579, dated Dec. 1, 2015, 6 pgs.

* cited by examiner

ASEPTIC PROCESSING WORKSTATION

This invention relates to an aseptic processing workstation.

In a number of applications, medical and pharmaceutical in particular, it is required that certain operations are carried out in a controlled sterile environment to enable medicines, pharmaceuticals, surgical instruments and the like to be handled in a manner which protects them from contamination. Some drugs, such as cytotoxic cancer drugs, are toxic and therefore need to be handled in such a manner to protect the operators from the hazardous effects thereof. The items therefore need to be handled in a system or unit which is completely closed and offers complete isolation of the items from the surrounding environment. The aseptic processing units which offer these facilities are known as Isolators. Isolators often incorporate chambers with glove attachments, to enable the operator to carry out manual operations inside the unit, such as the preparation of a pharmaceutical prescription.

Isolators can be supplied with filtered air to maintain the sterility of the processing chamber during the aseptic process. The isolators which are in common use today may be ducted or of the re-circulatory type, in either a turbulent or laminar flow configuration and generally require at least one fan on the inlet or outlet to control the pressure and/or flow. Typical configurations of Isolator designs in current use are given in FIGS. 4, 5 and 6.

FIG. 4 is a schematic showing airflow within a recirculatory laminar flow Isolator; FIG. 5 is a schematic showing the airflow of a once-through turbulent flow Isolator; and FIG. 6 provides a schematic showing airflow within a once-through laminar flow Isolator.

Isolators with an integrated bio-decontamination system are known, for example the PSI Isolator supplied by Skan AG which uses Hydrogen Peroxide ($H_2O_2$) as the decontaminant. It has a work chamber connected to an airlock, both of which are hermetically sealed against the surrounding environment and can be decontaminated individually.

Another such Isolator is the ISOCYT FREJA system supplied by Getinge La Calhene.

Due to space (particularly height) and other restrictions, i.e. energy, in the type of locations in which Isolators are commonly used, e.g. pharmacies, pharmaceutical facilities, laboratories and the like, it is desirable that they are able to run as either a positive or a negative pressure system without having to modify the hardware. In addition it is desirable to control the airflow and pressure when working in both 'normal' operating mode, in which a proportion of the airflow is made up of fresh incoming air, and when operating in a 100% re-circulatory mode, in which a significant amounts of air cannot be removed or added to the enclosure. It is desirable to control the pressure and airflow in re-circulatory mode; when running a decontamination cycle to contain the sterilant, distribute it (gassing phases), and remove it.

The invention therefore provides an aseptic processing workstation that aims to provide these benefits.

According to the invention there is therefore provided an aseptic processing workstation comprising a processing chamber; an airflow circuit passing through the chamber, said circuit comprising an air supply fan, an air return fan and a restriction element, the chamber being located in the circuit between the air supply fan and the air return fan, and the restriction element being located in the circuit on the other side of the air supply fan and the air return fan to the chamber; an air inlet fluidly connected at a first connection point to the circuit via inlet valve means, the first connection point being located between the restriction element and the air supply fan; an air outlet fluidly connected at a second connection point to the circuit via outlet valve means; and control means for independently controlling the speed of the air supply fan and the air return fan.

The invention therefore provides an aseptic processing workstation in which the pressure in the chamber and airflow can be controlled by adjustment of fan velocity; creating a pressure drop across a restriction which is mirrored within the chamber. This can be achieved both when there is a proportion of the air being fresh air, and also when the system is working in re-circulatory mode.

Therefore, by means of control logic the chamber pressure and airflow can be controlled by adjustment of the fan speeds without any hardware configuration changes and minimal use of an independent pressure control system.

This is achieved by means of fans which are located either side of a restriction in the airflow circuit. The invention also provides energy savings and a means of providing a more compact arrangement over the prior art Isolators.

The aseptic processing workstation further comprises at least one filter means located between the air inlet and the first connection point and at least one filter means located between the air outlet and the second connection point.

The valve means are preferably operable to run the aseptic processing workstation in a recirculatory mode with substantially all of the air remaining in, and being recirculated through, the circuit.

The valve means are also operable to run the aseptic processing workstation in a normal mode in which a proportion of the air being circulated is fresh air drawn in via the air inlet.

Preferably the airflow of the supply fan and the return fan are independently adjustable to vary the pressure in the chamber and vary the air flow through the chamber.

The airflow of the supply fan and the return fan may be independently adjustable to provide either a positive or a negative pressure in the chamber.

The restriction element may be a filter or an orifice. Preferably the restriction element is used to remove the sterilant.

A preferred embodiment of the present invention will now be described, by way of example only, in which:—

The invention relates to an aseptic processing workstation, such as an Isolator, with an integrated bio-decontamination system utilising Hydrogen Peroxide ($H_2O_2$) as the decontaminant.

Figure 1:
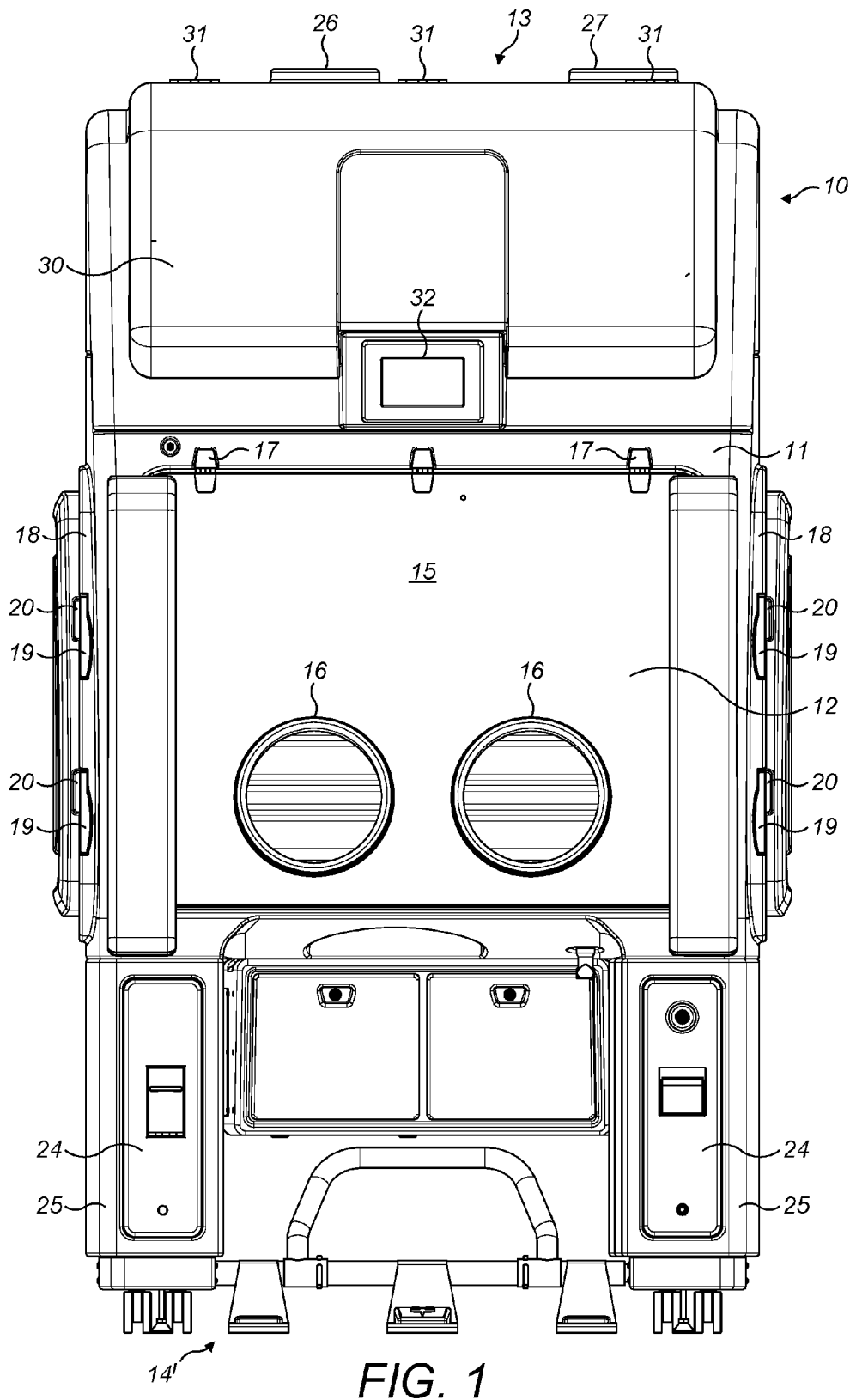
FIG. 1 is front elevation of an aseptic processing workstation according to the invention.

Referring to FIG. 1, this shows one embodiment of such an aseptic processing workstation 10 which is capable of being operated in a 'normal' operating mode, in which a proportion of the airflow is made up of fresh incoming air, and a 100% recirculatory mode, in which a significant amount of air cannot be removed or introduced into the workstation 10.

The workstation 10 has a modular housing 11, which has a processing chamber 12 located between an upper section 13 and a lower section 14. The housing 11 is preferably manufactured from a suitable plastic or stainless steel material which will withstand the decontaminant used (such as $H_2O_2$).

The processing chamber 12 has a front opening, which is closed by means of a panel 15, preferably made of a transparent plastic or glass. The panel 15 has a pair of apertures 16 to which are attached gloves (not shown) to enable an operator to safely manipulate the contents of the chamber 12. The edges of the gloves are therefore hermetically sealed to the peripheries of the apertures 16 in a known manner.

The panel 15 is attached to the housing 11 by one or more hinges 17 provided at the top edge of the panel 15 so that the panel 15 can be pivoted between a closed and an open position. One or more actuators 18, such as gas struts, are connected between one or both side edges of the panel 15 and the housing 11 to facilitate the opening of the panel 15 and to enable it to be supported in an open position. Seals are provided around the periphery of the opening, so that when the panel 15 is closed, the processing chamber 12 is hermetically sealed.

Figure 4:
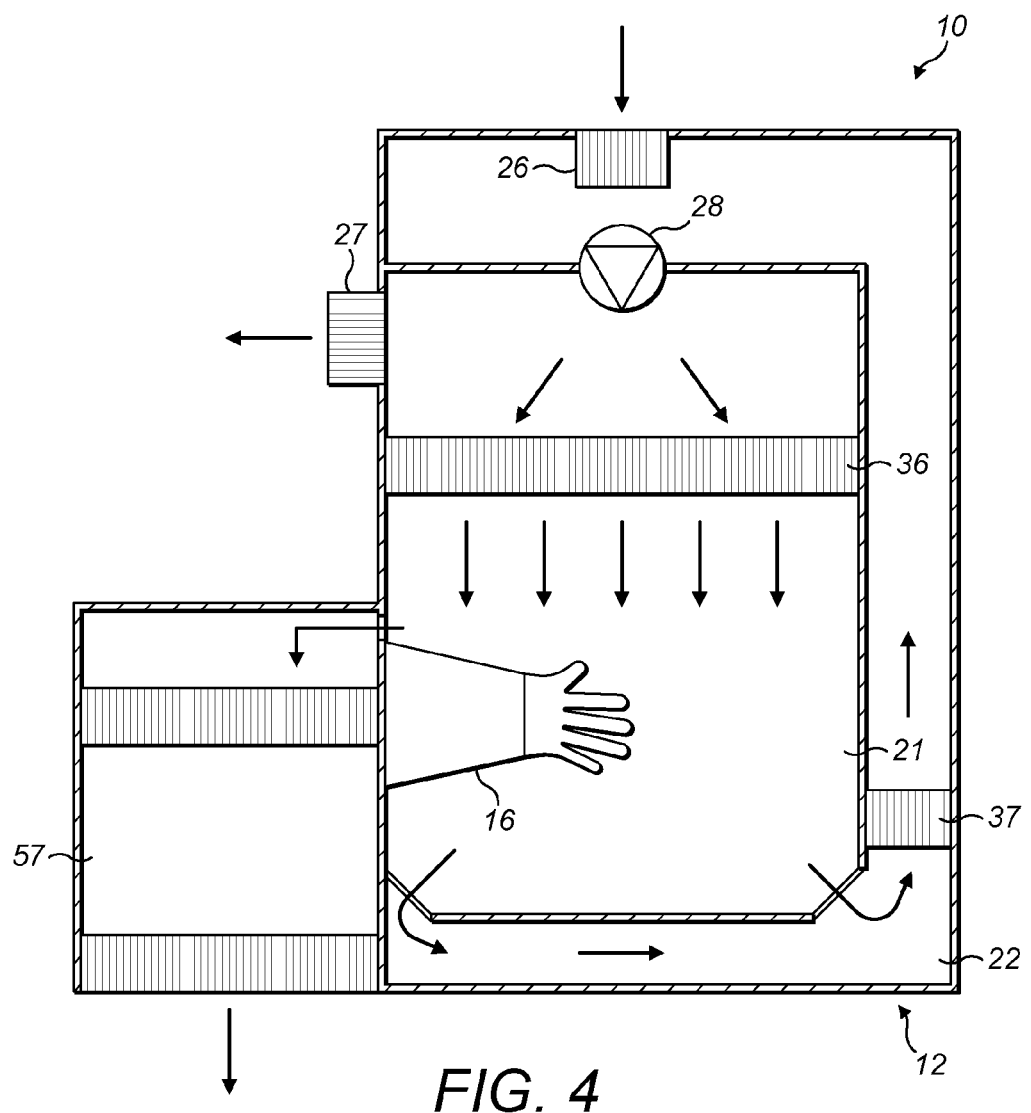
FIGS. 4 to 6 are typical configurations of prior art Isolator designs in current use.

The processing chamber 12 may have a working area and a plenum airspace which is above, behind and above the working area in a similar manner to the prior art Isolator illustrated in FIG. 4.

The processing chamber 12 may have only a single working area, or it may be divided into a plurality of working areas or there may be a plurality of linked processing chambers 12. A plurality of processing chambers 12 are linked, and/or one or more pass-out chambers or other types of extension modules.

The lower housing section 14 provides support for the processing chamber 12 and the upper section 13. In the embodiment illustrated the lower section 14 comprises a pair of legs 25, which may be arranged as cabinets, which preferably have opening doors 24, trays, slidable trays or drawers, in which is stored the decontaminant supply, such as a bottle of hydrogen peroxide ($H_2O_2$), and for housing system components and the like. Using the lower section 14 in this way helps to keep the centre of gravity of the workstation 10 low to keep it more stable.

The upper housing section 13 provides an air inlet 26 and an air outlet 27 into the workstation 10 and houses the air supply and air return fans, which are variable speed fans. The upper section has a front opening which is closed by means of a door 30. Preferably the door 30 is formed from a hinged access panel and a seal is provided by a further panel underneath the hinged access panel. The door is preferably attached to the housing 11 by one or more hinges 31 provided at the top edge of the door 30 so that the door 30 can be pivoted between a closed and an open position. A graphics display 32 may be mounted to the upper housing section 13 for displaying information to the workstation operator.

Figure 2:
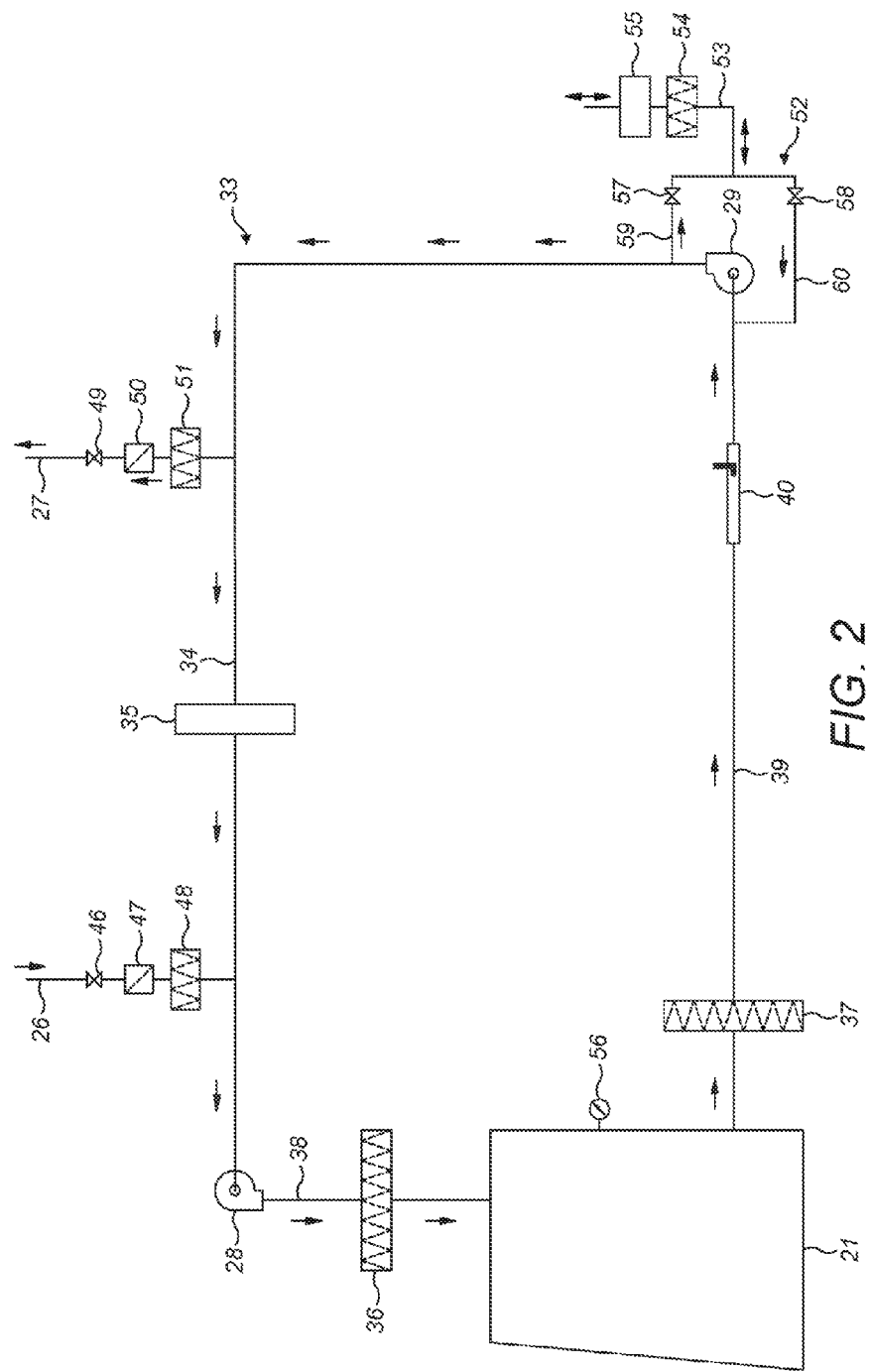
FIG. 2 is a schematic illustrating a first embodiment of the airflow in the aseptic processing workstation of FIG. 1.

Referring to FIG. 2, the air inlet 26 and the air outlet 27 are fluidly connected, at separate points, to an airflow circuit 33. The circuit 33 is formed from suitable conduits, and extends from the air supply fan 28, through the processing chamber 12 and back to the air supply fan 28. The air return fan 29 is also connected into the circuit 33. Located on a first section 34 of the circuit 33, between the points at which the air inlet 26 and the air outlet 27 are connected to the circuit, is a restriction element 35, which may be a catalytic (or other type of) filter or an orifice, which enables the creation of a pressure drop across it. When the restriction element 35 is a filter, this may advantageously be used to facilitate the removal of the sterilant.

An inlet boundary filter 36 is provided in a second section 38 of the circuit 33, which extends between the air supply fan 28 and the processing chamber 12, and which filters particulate from the air immediately before entry into the processing chamber 12. An outlet boundary filter 37 is provided in a third section 39 of the circuit 33, which extends between the processing chamber 12 and the air return fan 29, and which filters any particulate that has been shed by items within the chamber immediately after it has exited the processing chamber 12. A flow monitor 40 is also located in the third section 39 of the circuit 33. Control logic based upon the output of the flow monitor may be used to determine fault conditions within the system, i.e. blocked filter.

The air inlet 26 comprises an inlet valve 46, for controlling the flow of ambient air into the workstation 10, and one or more inlet filters 47, 48. Filter 47 may be a pre-filter and filter 48 may be a HEPA filter.

The air outlet 27 comprises an outlet valve 49, for controlling the flow of air out of the workstation 10 being exhausted to atmosphere, and one or more exhaust filters 50, 51. Filter 50 may be a pre-filter and filter 51 may be a HEPA filter.

The inlet and outlet valves 46, 49 are preferably two-position (open or closed) valves.

A leak test circuit 52 may be connected into the circuit 33 across the air return fan 29. This enables the circuit 33 to be tested for leaks and to allow air to be drawn into the circuit 33. An inlet conduit 59 is connected downstream of the air return fan 29 and an outlet conduit 60 is connected upstream of the air return fan 29. Connected in between the inlet and outlet conduits 59, 60 is an inlet/exhaust conduit 53, which is provided with one or more filters 54, 55. Air can flow in either direction through inlet/exhaust conduit 53 and filters 54, 55. Filter 55 may be a catalytic filter if sterilant vapour is exhausted, and filter 54 may be a HEPA filter. One or more valves 57, 58 may be provided to control the flow of air into and out of the leak test circuit 52. Preferably, the first valve 57 is opened to enable air to be exhausted through the inlet/exhaust conduit 53. The second valve 58 is opened to enable air to be drawn into the circuit 52 through the inlet/exhaust conduit 53.

Figure 3:
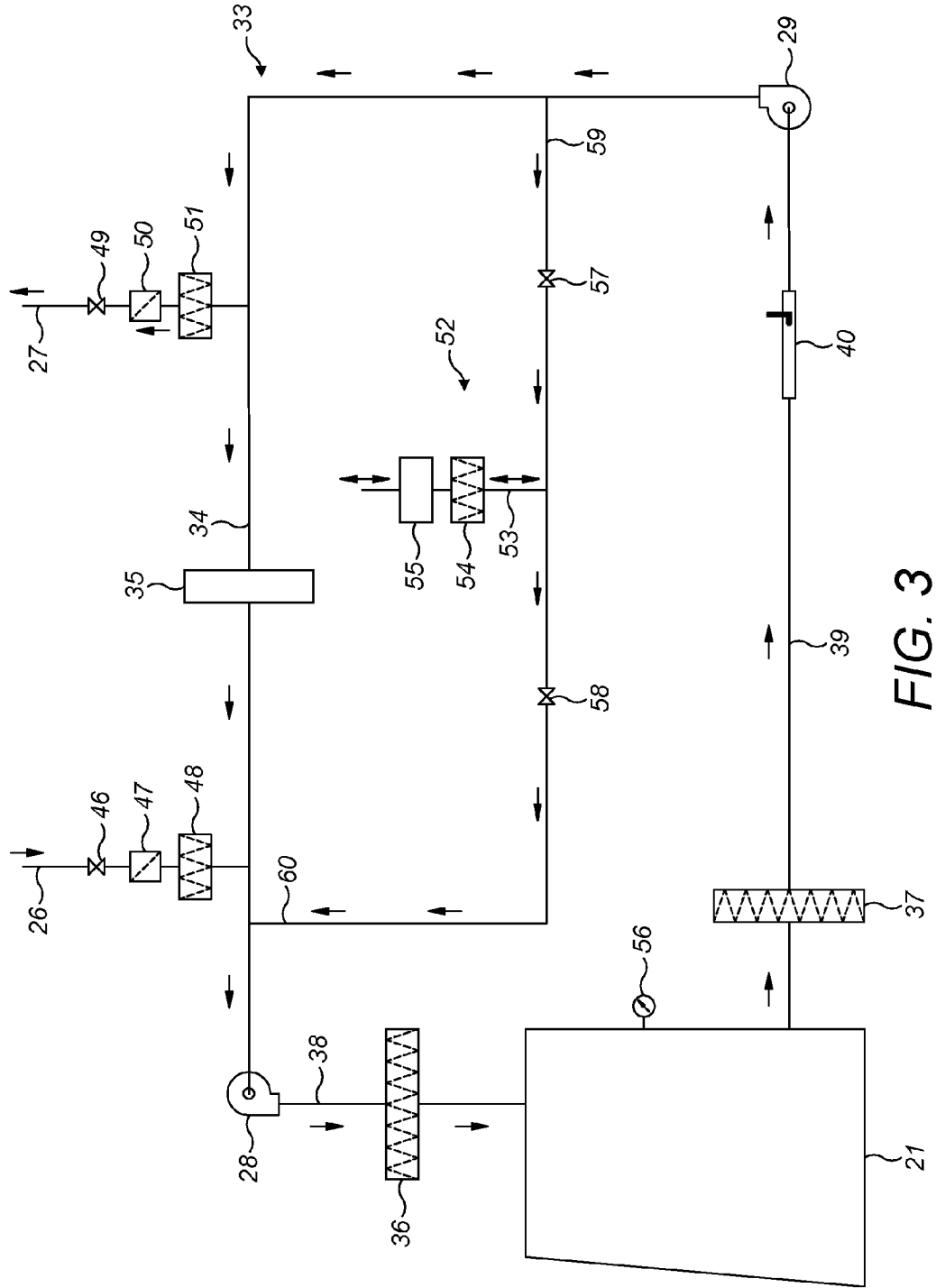
FIG. 3 is a schematic illustrating a second embodiment of the airflow in the aseptic processing chamber of FIG. 1.

Alternatively, as shown in FIG. 3, the air leak test circuit 52 may be connected into the circuit 33 across the restriction element 35. In a particular embodiment, the inlet conduit 59 to the air leak test circuit is connected to the circuit 33 in between the air return fan 29 and the air outlet 27. The outlet conduit 60 is connected to the circuit 33 in between the air inlet 26 and the air supply fan 28. The inlet/exhaust conduit 53 is connected to the air leak test circuit 52 in between two valves 57, 58.

The third section 39 of the circuit 33 is generally also housed in the upper housing section 13 along with the air supply and return fans 28, 29 and the restriction element. The air supply and return filters 36, 37 are located at suitable locations of the processing chamber 12 where the air enter and exits the processing chamber 12 respectively.

The pressure in the processing chamber 12 is monitored by means of a pressure gauge 56, the output of which is used by the control system.

The aseptic processing workstation 10 further comprises control electronics for controlling the operation of the fans 28, 29 to thereby alter the airflow and the pressure in the processing chamber 12.

The aseptic processing workstation 10 may optionally be provided with a pass out chamber (similar to that depicted in FIG. 4). The function of a pass-out chamber is to ensure that items can be safely passed into and/or out of the processing chamber 12. It is preferably a Type D transfer device to ISO14644-7 in that it comprises one door that opens to an adjoining chamber and another door that opens to the room, which is attached to one side of the processing chamber 12 with a sealable opening there between. The air flow in the pass out chamber may be controlled separately from the air flow circuit 33.

Figure 5:
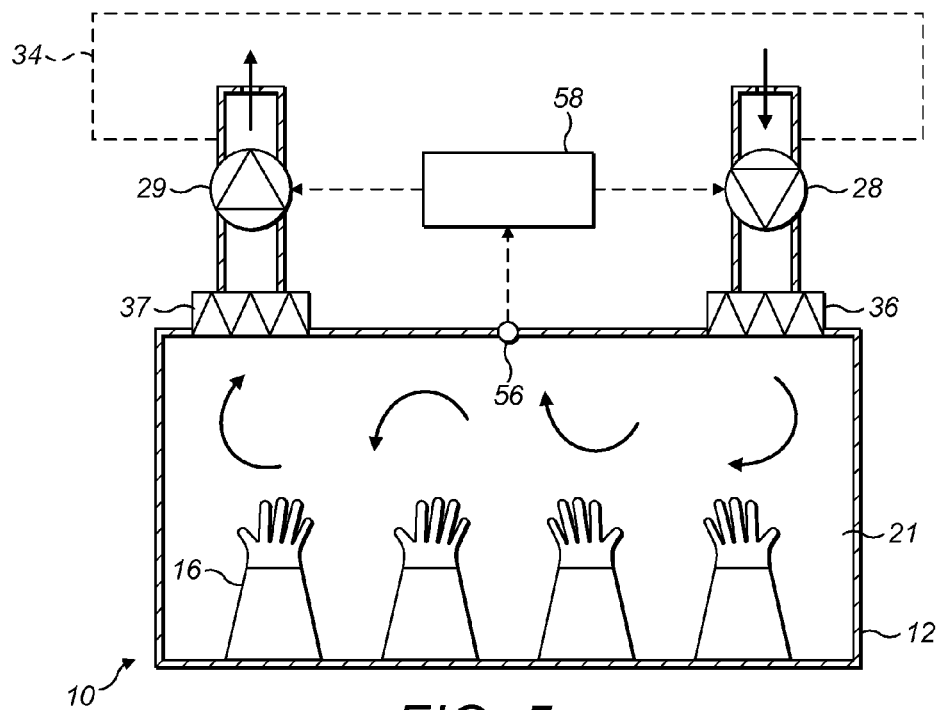
Figure 6:
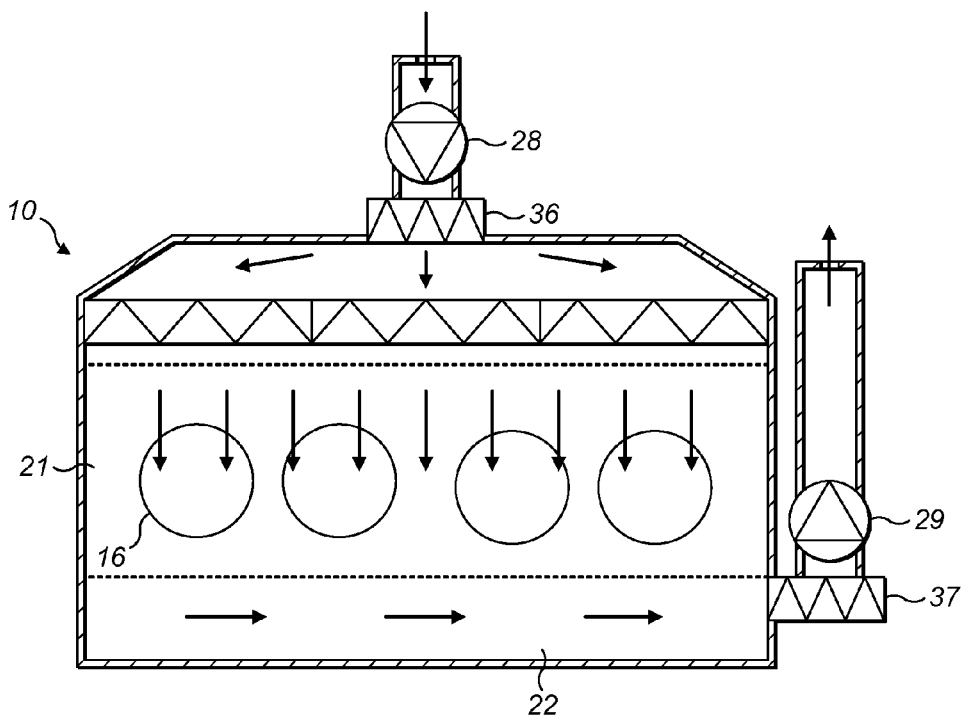

The aseptic processing workstation 10 is preferably provided with an integrated bio-decontamination system comprising a vaporiser for vaporising the decontaminant for circulation in the airflow This invention is operable in closed or open loop configuration (as shown in the prior art Isolators illustrated in FIGS. 4, 5 and 6) and for enclosures running negative or positive pressure.

The control system enables operation of the aseptic processing workstation 10 in either normal or recirculatory mode and alters the settings of the inlet and outlet valves 46, 49 accordingly.

When one fan 28, 29 rotates faster than the other a pressure differential is created across the restriction 35 that is mirrored in the chamber/enclosure 12 When the aseptic processing workstation 10 is running in normal mode, the airflow of the supply and return fans 28, 29 can be adjusted to alter the air velocity and the pressure within the processing chamber 12 by creating the pressure drop across the restriction element 35. It is thus possible to create any desired pressure at a given air flow set point by adjusting the fans only. This is achieved by means of control logic and the controller is typically a proportional integral derivative (PID) controller. The velocity of the airflow through the processing chamber 12 is typically in the region of 0.25 to 0.45 m/s.

The arrangement of the air supply and return fans 28, 29 in the circuit 33 on either side of the restriction 35 (as opposed to in the air inlet 26 and air outlet 27 with a single fan as shown in FIG. 4 or other variations and combinations as configured at present in known isolators) provides the advantage that the chamber 12 can be run in both normal percentage fresh-air introduction mode and in Recirculatory mode where the chamber pressure and airflow is controlled predominantly by the fan speeds.

The invention claimed is:

1. An aseptic processing workstation comprising:
   a processing chamber;
   an airflow circuit passing through the chamber, said circuit comprising an air supply fan, an air return fan and a restriction element, the chamber being located in the circuit between the air supply fan and the air return fan, and the restriction element being located in the circuit on the other side of the air supply fan and the air return fan to the chamber;
   an air inlet fluidly connected at a first connection point to the circuit via an inlet valve, the first connection point being located between the restriction element and the air supply fan;
   an air outlet fluidly connected at a second connection point to the circuit via an outlet valve; and
   a controller for independently controlling the speed of the air supply fan and the air return fan.

2. An aseptic processing workstation as claimed in claim 1 further comprising at least one filter located between the air inlet and the first connection point and at least one filter located between the air outlet and the second connection point.

3. An aseptic processing workstation as claimed in claim 1, wherein the valves are operable to run the aseptic processing workstation in a recirculatory mode with substantially all of the air remaining in, and being recirculated through, the circuit.

4. An aseptic processing workstation as claimed in claim 1, wherein the valves are operable to run the aseptic processing workstation in a normal mode in which a proportion of the air being circulated is fresh air drawn in via the air inlet.

5. An aseptic processing workstation as claimed in claim 1, wherein the airflow of the supply fan and the return fan are independently adjustable to vary the pressure in the chamber and vary the air flow through the chamber.

6. An aseptic processing workstation as claimed in claim 5 in which the airflow of the supply fan and the return fan are independently adjustable to provide either a positive or a negative pressure in the chamber.

7. An aseptic processing workstation as claimed in claim 1, wherein the restriction element is a filter.

8. An aseptic processing workstation as claimed in claim 1 wherein the restriction element is an orifice.

9. An aseptic processing workstation as claimed in claim 7 wherein the filter is operable to remove a sterilant from air circulating in the aseptic processing workstation.

10. An aseptic processing workstation as claimed in claim 2, wherein the valves are operable to run the aseptic processing workstation in a recirculatory mode with substantially all of the air remaining in, and being recirculated through, the circuit.

11. An aseptic processing workstation as claimed in claim 2, wherein the valves are operable to run the aseptic processing workstation in a normal mode in which a proportion of the air being circulated is fresh air drawn in via the air inlet.

12. An aseptic processing workstation as claimed in claim 3, wherein the valves are operable to run the aseptic processing workstation in a normal mode in which a proportion of the air being circulated is fresh air drawn in via the air inlet.

13. An aseptic processing workstation as claimed in claim 2, wherein the airflow of the supply fan and the return fan are independently adjustable to vary the pressure in the chamber and vary the air flow through the chamber.

14. An aseptic processing workstation as claimed in claim 3, wherein the airflow of the supply fan and the return fan are independently adjustable to vary the pressure in the chamber and vary the air flow through the chamber.

15. An aseptic processing workstation as claimed in claim 4, wherein the airflow of the supply fan and the return fan are independently adjustable to vary the pressure in the chamber and vary the air flow through the chamber.

16. An aseptic processing workstation as claimed in claim 5, wherein the restriction element is a filter.

17. An aseptic processing workstation as claimed in claim 6, wherein the restriction element is a filter.

18. An aseptic processing workstation as claimed in claim 17 wherein the filter is operable to remove a sterilant from air circulating in the aseptic processing workstation.

19. An aseptic processing workstation as claimed in claim 5, wherein the restriction element is an orifice.

20. An aseptic processing workstation as claimed in claim 6, wherein the restriction element is an orifice.

* * * * *